(12) United States Patent
Mo et al.

(10) Patent No.: US 9,797,937 B2
(45) Date of Patent: Oct. 24, 2017

(54) SYSTEMS AND METHODS UTILIZING CARBON NANOFIBER AGGREGATE FOR PERFORMANCE MONITORING OF CONCRETE STRUCTURES

(71) Applicants: Yi-Lung Mo, Pearland, TX (US); Rachel Howser, Houston, TX (US); Hermant Dhonde, Pune (IN); Gangbing Song, Pearland, TX (US)

(72) Inventors: Yi-Lung Mo, Pearland, TX (US); Rachel Howser, Houston, TX (US); Hermant Dhonde, Pune (IN); Gangbing Song, Pearland, TX (US)

(73) Assignee: UNIVERSITY OF HOUSTON, Houston, TX (US)

( * ) Notice: Subject to any disclaimer, the term of this patent is extended or adjusted under 35 U.S.C. 154(b) by 837 days.

(21) Appl. No.: 14/058,547

(22) Filed: Oct. 21, 2013

(65) Prior Publication Data
US 2014/0111231 A1    Apr. 24, 2014

Related U.S. Application Data

(60) Provisional application No. 61/716,301, filed on Oct. 19, 2012.

(51) Int. Cl.
*G01R 27/02* (2006.01)
*D04B 21/10* (2006.01)
(Continued)

(52) U.S. Cl.
CPC .......... *G01R 27/14* (2013.01); *B28B 17/0072* (2013.01); *G01M 5/0041* (2013.01);
(Continued)

(58) Field of Classification Search
CPC .... G01R 27/14; B29C 39/003; G01M 5/0041; G01M 5/0083; Y10T 442/10; C04B 40/00; C04B 40/0046; C04B 40/0028
(Continued)

(56) References Cited

U.S. PATENT DOCUMENTS

| 4,506,250 A | 3/1985 | Kirby |
| 5,817,944 A | 10/1998 | Chung |

(Continued)

FOREIGN PATENT DOCUMENTS

WO    WO 2011/074930    6/2011

OTHER PUBLICATIONS

Rodriguez et al, Structural Behavior of Self-Consolidating Carbon Nanofiber Concrete, Aug. 2010.
(Continued)

*Primary Examiner* — Melissa Koval
*Assistant Examiner* — Courtney McDonnough
(74) *Attorney, Agent, or Firm* — Winstead PC

(57) ABSTRACT

A carbon nanofiber aggregate (CNFA) system and method provides self-sensing capabilities that can be used to detect strain, moisture, and temperature changes. The CNFA may include cement, aggregate, silica fume, high-range water reducer (HRWR), and/or carbon nanofibers. The metal meshes in the CNFA may be utilized to monitor the electric properties of the CNFA to detect strain, moisture, and temperature changes. The CNFA may be embedded in concrete structures to allow detection of strain, moisture, and temperature changes that may cause damage to structures. Several metal meshes may be embedded in the CNFA.

16 Claims, 16 Drawing Sheets

(51) Int. Cl.

| | |
|---|---|
| H01B 1/24 | (2006.01) |
| G01R 27/14 | (2006.01) |
| B28B 17/00 | (2006.01) |
| G01M 5/00 | (2006.01) |
| G01N 27/04 | (2006.01) |
| G01N 33/38 | (2006.01) |

(52) U.S. Cl.
CPC ........ *G01M 5/0083* (2013.01); *G01N 27/041* (2013.01); *G01N 33/383* (2013.01); *Y10T 442/10* (2015.04)

(58) Field of Classification Search
USPC ............................... 324/705; 442/1; 264/105
See application file for complete search history.

(56) References Cited

U.S. PATENT DOCUMENTS

| | | |
|---|---|---|
| 7,666,327 B1 | 2/2010 | Veedu |
| 7,921,727 B2 | 4/2011 | Rice |
| 2010/0045311 A1 | 2/2010 | Chung |

OTHER PUBLICATIONS

Chung, Cement reinforced with sort carbon fibers: a multifunctional material. Elsevier Dec. 1999.
Wen et al, Effect of Moisture opn Plezoresistivity of Carbon Fiber-Reinforced Cement Paste, ACI Materials Journal, Jun. 2008.
Tyson et al, Carbon Nanotubes and Carbon Nanofibers for Enhancing the Mechanical Properties of Nanocomposite Cementitious Materials, ASCE, Jul. 2011.
PCT International Search Report and Written Opinion, PCT/US2013/-65899, dated Mar. 20, 2014.
R. N. Howser, H.B. Dhonde and Y. L. Mo, "Self-sensing of carbon nanofiber concrete columns subjected to reversed loading", Smart Materials and Structures, vol. 20, No. 8, 2011.
S. Iijima, "Helical microtubules of graphitic carbon", Nature, vol. 354, pp. 56-58, Nov. 7, 1991.
K.T. Lau and D. Hui, "The revolutionary creation of new advanced materials—carbon nanotube composites", Composites: Part B, vol. 33, No. 4, pp. 263-277, 2002.
Q. Ngo, A. M. Cassell, A. J. Austin, J. Li, S. Krishnan, M. Meyyappan and C. Y. Yang, "Characteristics of Aligned Carbon Nanofibers for Interconnect Via Applications", IEEE Electron Device Letters, vol. 27, No. 4, pp. 221-224, Apr. 2006.
F. Sanchez and K. Sobolev, "Nanotechnology in concrete—A Review", Construction and Building Materials, vol. 24, pp. 2060-2071, 2010.
P. W. Chen and D. D. L. Chung, "Concrete as a new strain/stress sensor", Composites Part B: Engineering, vol. 27. No. 1, pp. 11-23, 1996.
D. D. L. Chung, "Cement-matrix composites for smart structures", Smart Materials and Structures, vol. 9. No. 4, pp. 389-401, 2000.
P. W. Chen and D. D. L. Chung, "Concrete reinforced with up to 0.2 vol% of short carbon fibres", Composites, vol. 24, No. 1, pp. 33-52, 1993.
H. Li, H-g. Xiao, J. Yuan and J. Ou, "Microstructure of cement mortar with nano-particles", Composites Part B: Engineering, vol. 35, No. 2, pp. 185-189, Mar. 2004.
H. Li, M.-h. Zhang and J.-p Ou, "Abrasion resistance on concrete containing nano-particles for pavement:, Wear, vol. 260, No. 11-12, pp. 1262-1266, 2006.
H. Li, M.-h Zhang and J.-p Ou, "Flexural fatigue performance of concrete containing nano-particles for pavement", International Journal of Fatigue, vol. 29, No. 7, pp. 1292-1301, Jul. 2007.
D. D. L. Chung, "Strain sensors based on the electrical resistance change accompanying the reversible pull-out of conducting short fibers in a less conducting matrix", Smart Materials and Structures, vol. 4, No. 1, pp. 59-61, 1995.
H. Xiao, C. Lan, X. Ji and H. Li, "Mechanical and sensing properties of structural materials with nanophase materials", Pacific Scientific Journal, vol. 5, pp. 11-17, 2003.
D. Gao, M. Strum and Y. L. Mo., "Electrical resistance of carbon-nanofiber concrete", Smart Materials and Structures, vol. 18, No. 9, pp. 1-7, 2009.
ACI Committee 318, "Building Code Requirements for Structural Concrete (ACI 318-08) and Commentary", American Concrete Institute, 2008.
Joseph A. Daczko, "Stability of Self-Consolidating Concrete, Assumed or Ensured?", Master Builders Inc., pp. 245-2351.
Hemant B. Dhonde, Y. L. Mo, Thomas T. C. Hsu and John Vogel, "Fresh and hardened Properties of Self-Consolidating Fiber-Reinforced Concrete", ACI Materials Journal, Technical Paper, Title No. 104-M54, pp. 491-500, 2007.
C. Foord and R. Gaimster, "Self-compacting concrete", Concrete, pp. 23-25, Apr. 2000.
K. H. Khayat, C. Hu and H. Monty, "Stability of Self-Consolidating Concrete, Advantages and Potential Applications", 1st International RILEM Symposium on Self-Compacting Concrete; Stockholm, Swede, Sep. 13-14, 1999, pp. 132-152.
Wen-Cheng Liao, Shih-Ho Chao, Sang-Yeol Park, Antonien, E. Naaman, "Self-Consolidating High Performance Fiber Reinforced Concrete (SCHPFRC-Preliminary Investigation)", Department of Civil and Environmental Engineering, University of Michigan, Dec. 2006.
H. Okamura and K. Ozawa, "Mix-Design for Self-Compacting Concrete", Concrete Library of the Japanese Society of Civil Engineers, vol. No. 25, Jun. 1995, pp. 107-120.
S. P. Shah and A. E. Naaman, "Mechanical Properties of Glass and Steel Fiber Reinforced Mortar", ACI Journal, vol. 73, pp. 50-53, 1976.
K. Tanaka, K. Sato, S. Watanabe, I. Arima and K. Seunaga, "Development and Utilization of High-Performance Concrete for the Construction of the Akashi Kaikyo Bridge", High Performance Concrete, vol. 140, pp. 25-52, 1993.
C. Li Victor, "Large Volume, High-Performance Applications of Fibers in Civil Engineering", Journal of Applied Polymer Science, vol. 83, pp. 660-686, 2002.
D. D. L. Chung, "Dispersion of Short Fibers in Cement", Journal of Materials in Civil Engineering, ASCE 17, No. 4 pp. 379-383.

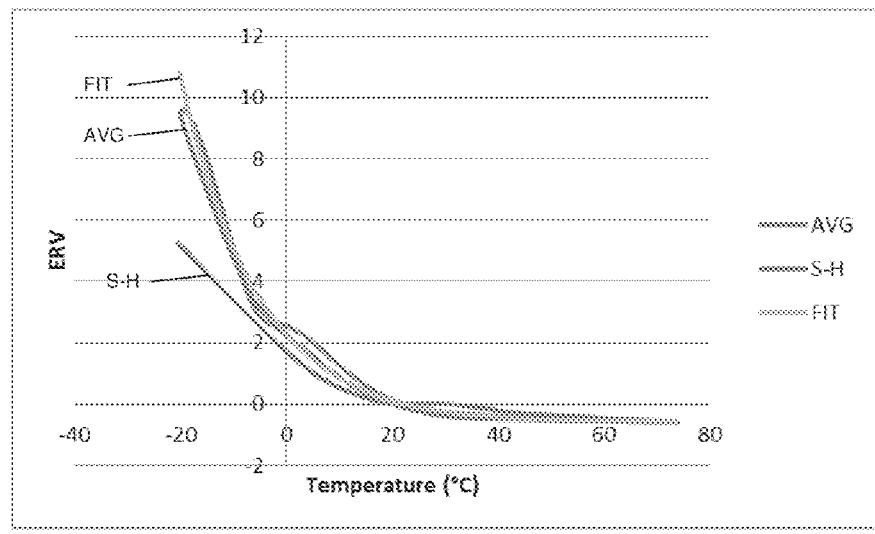
FIG. 32
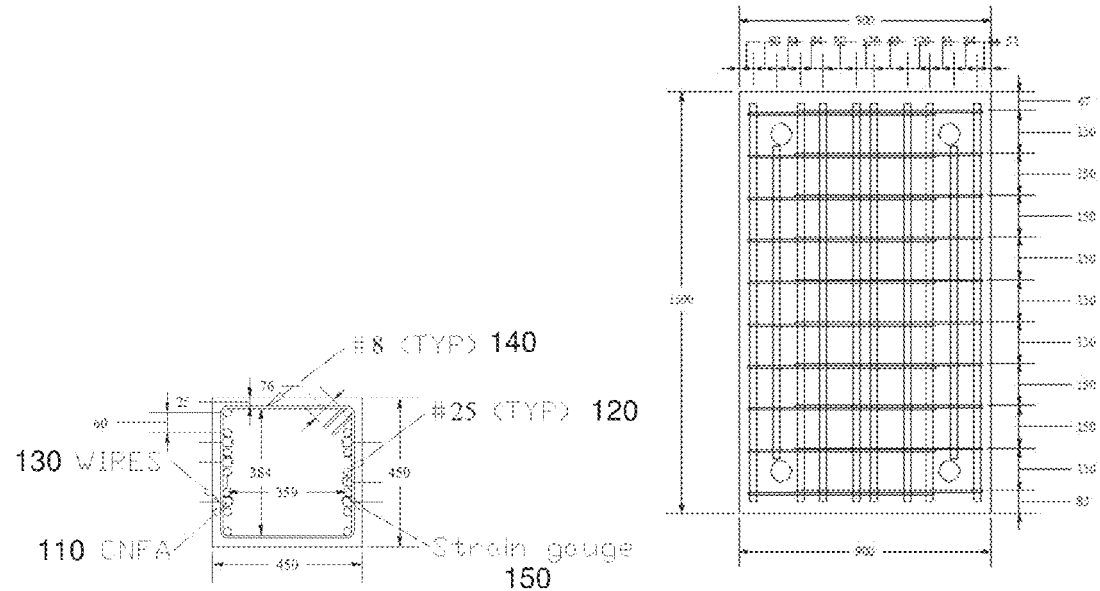
FIG. 33
FIG. 35

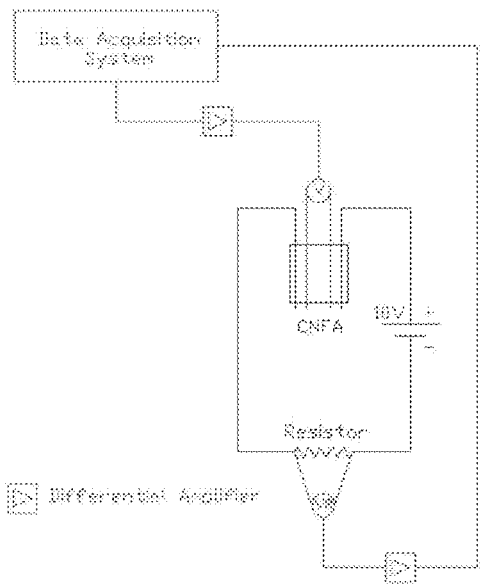
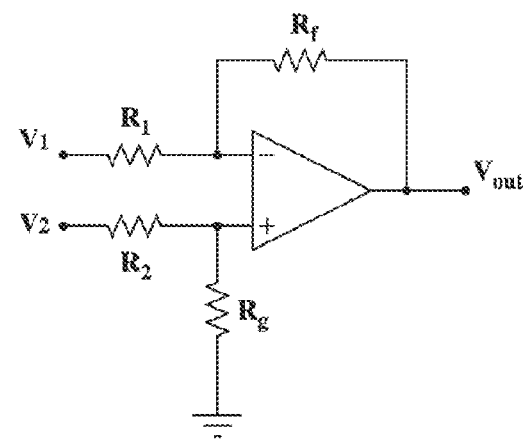
FIG. 40
FIG. 41
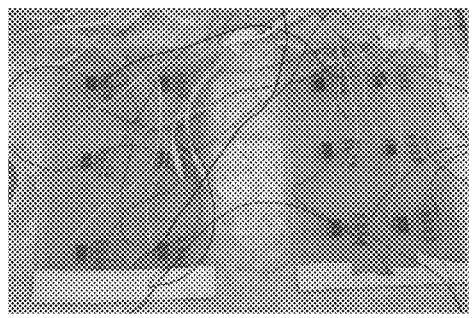
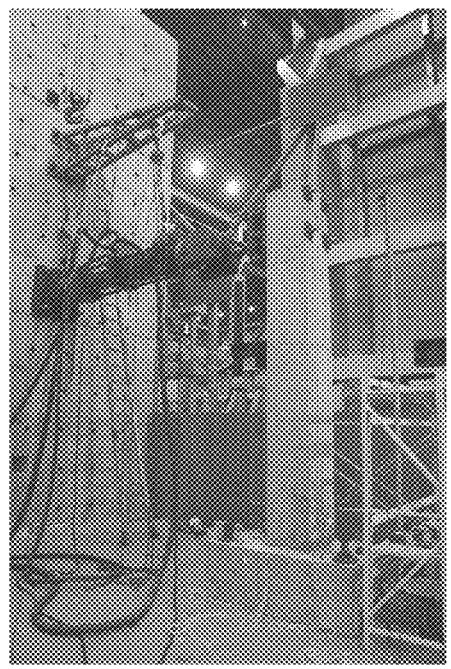
FIG. 42
FIG. 43

US 9,797,937 B2

SYSTEMS AND METHODS UTILIZING CARBON NANOFIBER AGGREGATE FOR PERFORMANCE MONITORING OF CONCRETE STRUCTURES

RELATED APPLICATIONS

This application claims the benefit of U.S. Provisional Patent Application No. 61/716,301 to Mo et al., filed on Oct. 19, 2012, which is incorporated herein by reference.

STATEMENT REGARDING SPONSORED RESEARCH

This invention was made with government support under Grant Number EEC-0634279 awarded by the National Science Foundation. The government has certain rights in the invention.

FIELD OF THE INVENTION

This invention relates to carbon nanofiber aggregate (CNFA) systems and methods. More particularly, to CNFA systems and methods for monitoring structural health, moisture, temperature changes, or combinations thereof in concrete structures.

BACKGROUND OF INVENTION

Carbon nanofiber (CNF) are graphene layers arranged as stacks of cones, cups or plates to create a cylindrical nanostructure. Carbon nanotubes (CNT) are graphene layers wrapped into perfect cylinders. CNF are easier to construct than CNT, making them up to 100 times cheaper and suitable for mass production. CNF also present numerous exposed edge places along their surface allowing better bond than their CNT counterparts. Most efforts have been concentrated on polymeric CNT/CNF composites due to dispersion problems. The results of adding carbon CNF to cement based materials has yielded mixed results. The successful addition of CNF to cement-based materials has many advantageous mechanical and electrical properties including increased strength, ductility, and conductivity.

Fiber research in concrete construction is an ongoing field. Short-fiber composites are a class of strain sensor based on the concept of short electrically conducting fiber pull-out that accompanies slight and reversible crack opening. For a fiber composite to have strain sensing ability, the fibers must be more conducting than the matrix in which they are embedded, have a diameter smaller than the crack length, and well dispersed. Their orientations can be random, and they do not have to touch one another. The electrical conductivity of the fibers enables the DC electrical resistivity of the composites to change in response to strain damage, moisture, or temperature, thereby making them suitable for sensing.

The structural behavior and self-sensing ability of concrete nanofibers aggregates (CNFA) allows for structural health monitoring for the reduction of maintenance and enhanced concrete construction. As a nonlimiting example CNFA can be used to monitor strain, water content, temperature changes, or combinations thereof in concrete structures.

SUMMARY OF THE INVENTION

In some embodiments, a carbon nanofiber aggregate (CNFA) system and method provides self-sensing capabilities that can be used to detect strain, moisture, and temperature changes. The CNFA may include cement, aggregate, silica fume, high-range water reducer (HRWR), and/or carbon nanofibers. In some embodiments, the CNFA may include equal to or less than 1.0% CNF by weight. In some embodiments, the CNFA may be approximately 0.7% CNF by weight. In some embodiments, the CNFA may be equal to or between 0.5 to 1.0% CNF by weight. The CNFA may be embedded in concrete structures to allow detection of strain, moisture, or temperatures that may cause damage to structures. Several metal meshes may be embedded in the CNFA. The metal meshes in the CNFA may be utilized to monitor the electric properties of the CNFA to detect strain, moisture, and temperature changes.

In another embodiment, a method for monitoring a structure comprises positioning a carbon nanofiber aggregate (CNFA) in a concrete structure, wherein the CNFA comprises a mixture of cement, aggregate, high-range-water reducer, carbon nanofibers (CNF), and metallic meshes positioned in the CNFA. In some embodiments, a current may be applied to a pair of metallic meshes, and a voltage change between a pair of metallic meshes may be monitored to determine a resistance based on the voltage change. In some embodiments, an electrical resistance variation (ERV) may also be determined. The resistance or ERV may be monitored to detect strain, moisture, changes in temperature, or combinations thereof.

In yet another embodiment, a method for forming a carbon nanofiber aggregate (CNFA) includes blending a first mixture of water, a High Range Water Reducer (HRWR), and carbon nanofibers (CNF); blending a second mixture of cement and aggregate; and combining and blending a first portion of the first mixture with the second mixture. The method may also include combining and blending a second portion of the first mixture with the second mixture; combining and blending a third portion of the first mixture with the second mixture form a final mixture; and positioning a plurality of metallic meshes in a formwork, wherein each of the plurality of metallic meshes is coupled to a wire, and the plurality of metallic meshes are secured in position by holes provided by the formwork. The final mixture is poured into the formwork, wherein the final mixture surrounds the plurality of metallic meshes, and the wires coupled to the plurality of metallic meshes extend out of the final mixture; and the final mixture is cured to harden the CNFA.

The foregoing has outlined rather broadly various features of the present disclosure in order that the detailed description that follows may be better understood. Additional features and advantages of the disclosure will be described hereinafter.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein:

FIG. 32 shows a comparison of Eureqa Fit, Steinhart-Hart equation and average measure ERV v. temperature for embedded CNFAs;

FIG. 33 shows an illustrative embodiment of a column cross-section (in mm);

FIG. 35 shows an illustrative embodiment of a foundation plan view (in mm);

FIG. 40 shows an illustrative embodiment of an electric circuit;

FIG. 41 shows an illustrative embodiment of a differential amplifier circuit;

FIG. 42 shows an illustrative embodiment of differential amplifiers;

FIG. 43 shows an illustrative embodiment of a column experiment setup;

DETAILED DESCRIPTION

Figure 1:
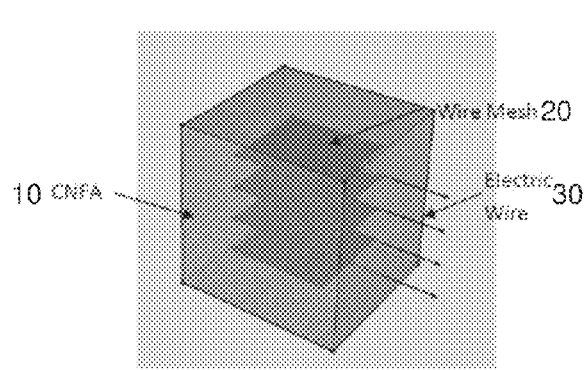
FIG. 1 is an illustrative embodiment of a concrete nanofiber aggregate (CNFA) schematic.

Refer now to the drawings wherein depicted elements are not necessarily shown to scale and wherein like or similar elements are designated by the same reference numeral through the several views.

Referring to the drawings in general, it will be understood that the illustrations are for the purpose of describing particular implementations of the disclosure and are not intended to be limiting thereto. While most of the terms used herein will be recognizable to those of ordinary skill in the art, it should be understood that when not explicitly defined, terms should be interpreted as adopting a meaning presently accepted by those of ordinary skill in the art.

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

Systems and methods utilizing carbon nanofiber aggregate (CNFA) for performance monitoring of concrete structures are discussed herein. The addition of CNF to cement-based materials has many advantageous mechanical and electrical properties. However, because of the high cost associated with carbon nanofiber (CNF), a CNF aggregate (CNFA) is desirable. In a nonlimiting embodiment, CNFA may include cement, a fine aggregate, silica fume, a high-range water reducer (HRWR), and/or carbon nanofibers. In a nonlimiting embodiment, the CNFA may include equal to or less than 1.0% CNF by weight. In a nonlimiting embodiment, the CNFA may be approximately 0.7% CNF by weight. In a nonlimiting embodiment, the CNFA may be equal to or between 0.5 to 1.0% CNF by weight. In a nonlimiting embodiment, the CNFA may be a cubic specimen of CNF mortar. The CNF mortar is self-sensing and can be used to detect strain, moisture, and/or temperature changes. The CNFA can be embedded in reinforced or prestressed concrete structures and used to determine the localized damage in a structure.

In an illustrative embodiment, the CNFA may provide one or more meshes. In some embodiments, the CNFA may provide four meshes. The meshes may be formed from a metal, such as steel or any other suitable metal. In some embodiments, a wire may be coupled to the mesh to provide an electric lead. The CNFA mixture may be formed around the mesh, such as by casting, to for a cubic CNFA specimen. The wires and meshes may be utilized to monitor changes in the electric properties of the CNFA, which correlate to changes strain, moisture, and/or temperature. In some embodiments, a power source may be provided to supply current to leads of the CNFA. In some embodiments, leads of the CNFA may be monitored with a voltmeter or the like to monitor electric properties of the CNFA. In embodiments providing four meshes, a four-point method may be utilized to measure electrical resistance. One or more cubic CNFA specimen may be embedded in a concrete structure to detect strain, moisture, and/or temperature.

Carbon Nanofiber Aggregates

CNF aggregate (CNFA) systems and methods discussed herein can be used to detect various parameters, including stress, strain, moisture, and temperature, in concrete structures. The development of a CNFA is significant because it is possible to use their strain sensing capabilities. The CNFA greatly reduced cost since only the CNFA placed in the structure would contain CNF. Self-consolidating carbon nanofiber concrete (SCCNFC) costs nearly 20 times as much as normal concrete.

In a nonlimiting embodiment, a CNFA may be 2.54 cm×2.54 cm×2.54 cm (1.00 in.×1.00 in.×1.00 in.) so that it is roughly the same size as a normal aggregate found in the concrete matrix. FIG. 1 shows a schematic of a proposed CNFA 10 using the four-point method for the measurement of electrical resistance. Four meshes 20 are distributed in the CNFA, and each of the meshes is positioned approximately parallel to the other meshes. An electric wire 30 is coupled to each of the four meshes 20, and the electric wires extend out of the CNFA. In other embodiments, it may be desirable to vary the size of the CNFA.

Electrical Resistance Measurement Technique

Figure 2:
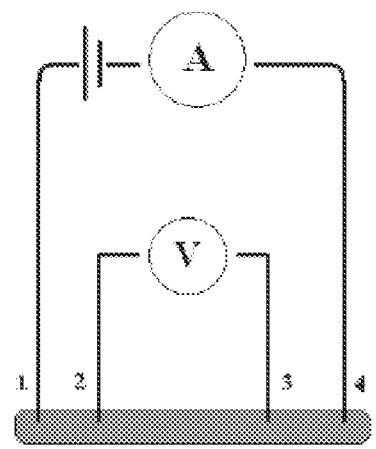
FIG. 2 is an illustrative embodiment of a four probe method for determining electrical resistance for a CNFA.

In some embodiments, a four probe method may be utilized to measure the electrical resistance variation in the CNFA specimens. In this method, current is supplied by a power supply to a pair of current leads, e.g. leads 1 and 4 in FIG. 2 representing wires connected to two outermost meshes in the CNFA. The voltage drop can be measured by a voltmeter or the like across the inner connections, e.g. leads 2 and 3 in FIG. 2 representing wires connected to two innermost meshes in the CNFA. Since the resistance of CNFA is much higher than the resistance of the wires, this method is quite accurate for determining the electrical resistance variation of the CNFA.

One can determine the resistance using Ohm's Law, V=RI Equation 3.1. The electrical resistance variation can be determined using Equation 3.2.

$$V = RI \qquad \text{Equation 3.1}$$

Where:
V: Voltage (V)
R: Resistance (Ω)
I: Current (A)

$$ERV = \frac{R_i - R_0}{R_0} \qquad \text{Equation 3.2}$$

Where:
ERV: Electrical Resistance Variation
$R_i$: Resistance at Step i
$R_0$: Initial Resistance CNFA Size In some embodiments, the size of the CNFA may be optimized for a desired application. The CNFA may be large enough so that the meshes required for the four probe method could be easily constructed and placed within the aggregate without touching one another. However, it may also be small enough to be aggregate sized. The CNFA may be appropriately sized so that it does not cause casting problems when it is embedded in a larger structure.

According the American Concrete Institute (ACI) (ACI 318 2008), the nominal maximum size of coarse aggregates should not be larger than:

a) ⅕ the narrowest dimension between sides of forms,
b) ⅓ the depth of slabs,
c) ¾ the minimum clear spacing between individual reinforcing bars or wires, bundles of bars, individual tendons, bundled tendons, or ducts.

However, these rules are not absolute in that the code allows that a licensed design professional may choose to use larger aggregates if the workability of the concrete and method of consolidation are adequate to eliminate honeycombing and voids.

In an exemplary embodiment, the aggregate size chosen was 2.54 cm by 2.54 cm by 2.54 cm (1.00 in. by 1.00 in. by 1.00 in). This allowed for both reasonable construction limitations as outlined by points a) through c) above and manageable space in which to place the four wire meshes needed for the four probe method.

Mesh Construction

Figure 3:
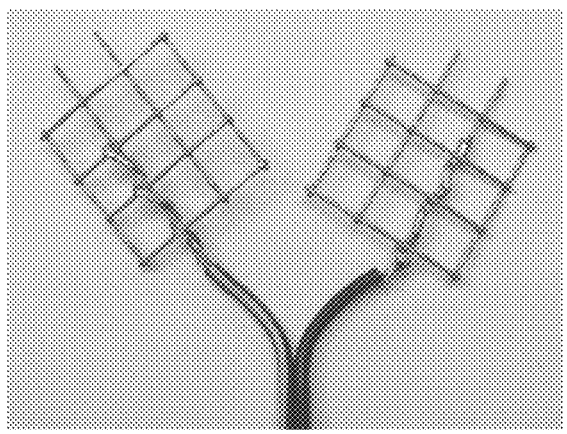
FIG. 3 is an illustrative embodiment of two meshes with wires.
Figure 4:
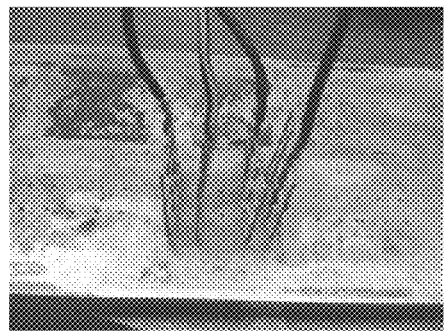
FIG. 4 is an illustrative embodiment of meshes inserted into formwork.
Figure 5:
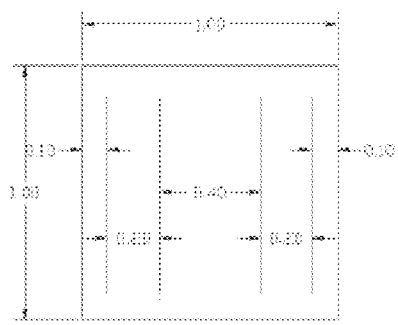
FIG. 5 is an illustrative embodiment of a mesh spacing (in inches)

In some embodiments, the CNFA may provide one or more meshes. In some embodiment, the CNFA may provide four meshes. In a nonlimiting embodiment, the meshes may be made from a metal hardware cloth. For example, the hardware cloth may be 6.35 mm by 6.35 mm (0.25 in. by 0.25 in.) 23 gauge welded galvanized steel hardware cloth. The hardware cloth may be cut into 19.05 mm by 19.05 mm (0.75 in. by 0.75 in.) squares with two prongs extending on one side and one prong extending on the opposite side as illustrated in FIG. 3. In some embodiments, the two extended prongs are inserted into holes drilled in the formwork to hold the meshes in place during casting as shown in FIG. 4. As shown, the meshes are positioned to be approximately parallel to each other. In some embodiments, the meshes are spaced as shown in FIG. 5. In some embodiments, the outermost meshes may be spaced 0.1 inches from the outer edge of the CNFA, and the innermost meshes may be space 0.2 inches from each the outermost meshes (or 0.3 inches from the outer edge of the CNFA) with a spacing of 0.4 inches between the two innermost meshes. The prong on the opposite side is used to reinforce the wire extending from the CNFA as this may be the most vulnerable place for the wire to break. For example, Gauge 24 copper wire was soldered to the meshes.

Mortar Mix Design

The CNFA includes a CNF mortar mix. In some embodiments, the properties of the materials used in the mix may be as follows:

a) Cement: For example, the cement used in all mixtures was ASTM Type I/II Portland cement in the testing discussed herein.

b) Fine Aggregate: For example, the fine aggregate used was Quikrete® Premium Play Sand, which is a washed, dried, and screened fine sand in the testing discussed herein.

c) High-Range Water Reducer (HRWR): For example, Glenium® 3400 HES is a polycarboxylate admixtures from BASF Chemical Co. in the testing discussed herein.

d) Carbon Nanofibers: For example, Pyrograf Products, Inc. PR-19-XT-LHT-OX fibers were used in the testing discussed herein. The specific gravity of the fibers is 0.0742. The diameter of the fibers is 149 nm (5.87e-6 in.) and the length is 19 μm (7.48e-4 in.) resulting in an aspect ratio of 128.

e) Pozzolanic materials (optional): Pozzolanic materials react with calcium hydroxide and water to form compounds possessing cementitious properties. For example, in the testing discussed herein, silica fume was utilized.

The following examples are included to demonstrate particular aspects of the present disclosure. It should be appreciated by those of ordinary skill in the art that the methods described in the examples that follow merely represent illustrative embodiments of the disclosure. Those of ordinary skill in the art should, in light of the present disclosure, appreciate that many changes can be made in the specific embodiments described and still obtain a like or similar result without departing from the spirit and scope of the present disclosure.

The mixture is preferably self-consolidating. Self-consolidating concrete (SCC) is highly flowable, non-segregating concrete that can spread into place, fill the formwork, and encapsulate the reinforcement without any mechanical consolidation. The mortar should flow under its own weight so that it flows around the meshes without creating voids and with no mechanical vibration. Further, measuring the electrical resistance variation (ERV) of the CNFA shows that it can provide a reversible damage sensor.

Figure 6:
FIG. 6 shows CNF clumps in mortar containing 1.75% CNF by weight.
Figure 8:
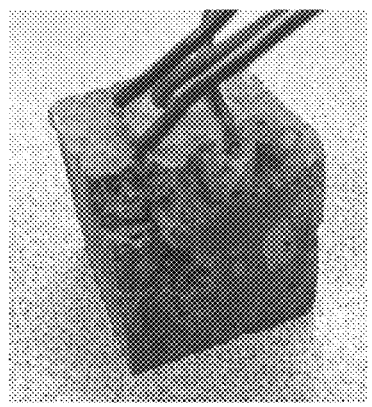
FIG. 8 shows severe damage in CNFA containing 1.75% CNF by weight due to clumping before testing.
Figure 7:
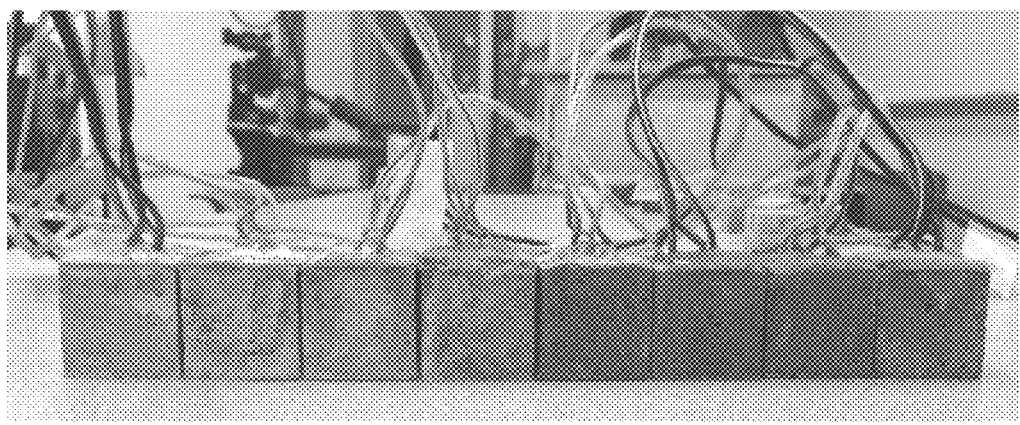
FIG. 7 shows color gradation of CNF mortar mixes (0.00%, 0.25%, 0.50%, 0.75%, 1.00%, 1.25%, 1.50%, and 1.75% CNF by weight)
Figure 9:
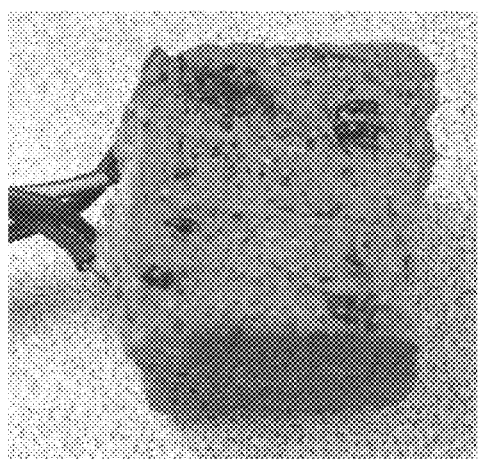
FIG. 9 shows CNF clump in tested CNFA containing 1.00% CNF by weight.

It has been discovered that at a concentration of 1.75% by weight of cement fiber clumping can be seen with the naked eye as shown in FIG. 6. FIG. 7 shows a series of CNFA with different CNF concentrations (i.e. 0.00%, 0.25%, 0.50%, 0.75%, 1.00%, 1.25%, 1.50%, and 1.75% by weight of cement). It can easily be seen that the color of the mortar becomes darker with each increase of CNF up to 1.75%. This is because of the severe clumping in the mortar mixture. CNFA containing 1.75% by weight of cement was damaged before testing due to the clumping as shown in FIG. 8. Visible clumps have been seen in tested CNFA containing 1.00% CNF by weight of cement as seen in FIG. 9. In some embodiments, concentration is equal to or less than 1.00% CNF by weight of cement. In some embodiments, concentration is in the range approximately equal to or between 0.5 to 1.00% CNF by weight of cement. In some embodiments, concentration is about 0.7% CNF by weight of cement.

Mortar Mixing Procedure

In some embodiments, the mixing procedure used for the CNFA is a hybrid of a mixing procedure for a high performance self-consolidating steel fiber reinforced concrete mix and a mixing procedure for a self-consolidating CNF concrete. For a high performance self-consolidating steel fiber reinforced concrete mix, the water and chemical admixtures were premixed and added to the cement, fly ash, and fine aggregates in several steps to create a homogenous paste before adding the coarse aggregate and fibers. For a self-consolidating CNF concrete, the water, chemical admixtures, and CNF were premixed and added the cement, fly ash, fine aggregates, and coarse aggregates in one step. An illustrative embodiment of a newly proposed mixing procedure is as follows. The mixing procedure is appropriate for small mortar mixes.

1) Pour the water, High Range Water Reducing superplasticizers (HRWR), and CNF into a laboratory grade blender and blend for 30 seconds.

Figure 10:
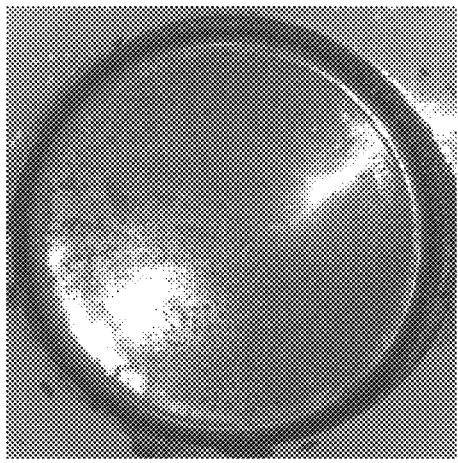
FIG. 10 shows an illustrative embodiment of a water, HRWR, and CNF mixture.

2) Remove the mixture and place into a separate container. FIG. 10 shows the water, HRWR, and CNF mixture.

3) Pour one half of the sand, all of the cement, then the rest of the sand into the blender. Dry mix for 30 seconds.

Figure 11:
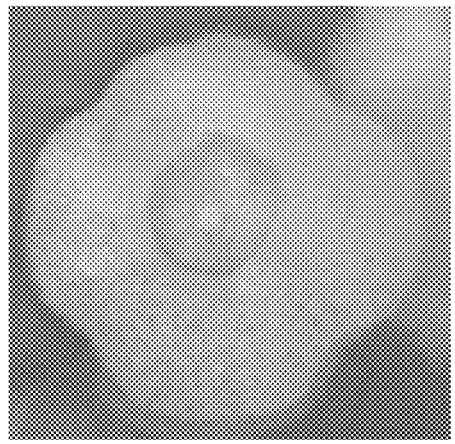
FIG. 11 shows an illustrative embodiment of sand and cement after a first dry mix.
Figure 12:
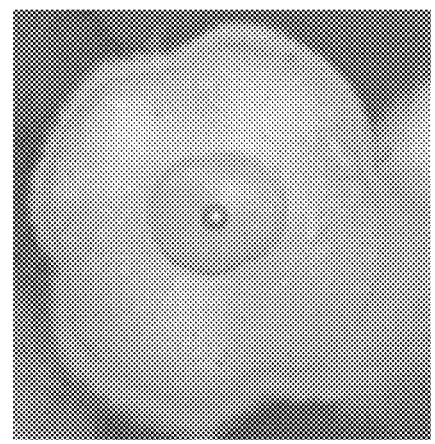
FIG. 12 shows an illustrative embodiment of cement and sand after a second dry mix.

4) Remove the blender from the stand. Use a long thin tool to scrape the sides and bottom of the blender. Place back onto the stand mix for 30 more seconds. FIG. 11 shows the sand and cement mixture after the first dry mix. FIG. 12 shows the sand and cement mixture after the second dry mix. It is easily seen that the mixture is much more homogenous after the second mix.

Figure 13:
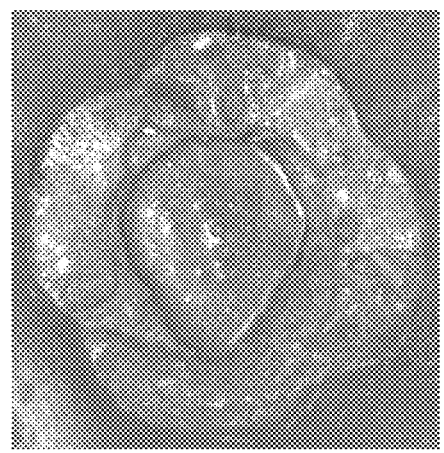
FIG. 13 shows an illustrative embodiment of a mortar mixture after first mixing (e.g. Step 5)
Figure 14:
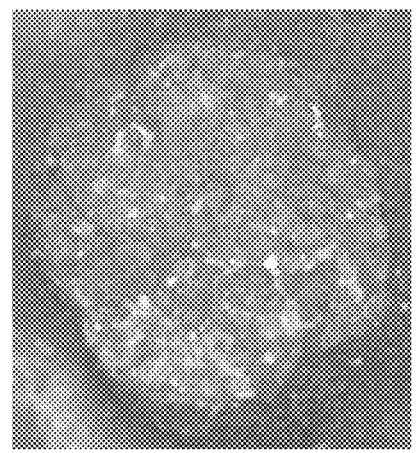
FIG. 14 shows an illustrative embodiment of a mortar mixture after second mixing (e.g. Step 5, Wet Granulated Sugar Stage)

5) Pour approximately one half of the water, HRWR, and CNF mixture to the sand and cement mixture. Mix for 30 seconds. FIG. 13 shows the mortar mixture after mixing. It can be seen that liquid is concentrated in the middle while the outside is mostly dry. Repeat Step 4. FIG. 14 shows the mixture after mixing the second time. The consistency of the mixture should be approximately that of wet granulated sugar.

Figure 15:
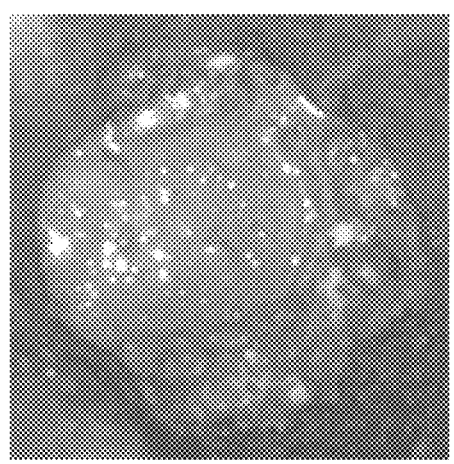
FIG. 15 shows an illustrative embodiment of a mortar mixture after first mixing (e.g. Step 6)
Figure 16:
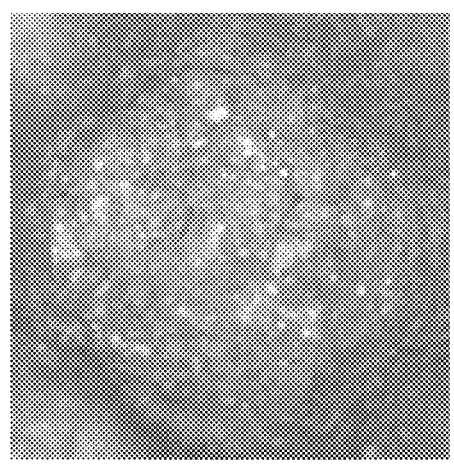
FIG. 16 shows an illustrative embodiment of a mortar mixture after second mixing (e.g. Step 6, Dough Stage)

6) Pour approximately one half of the remaining water, HRWR, and CNF mixture (one quarter of the total mixture) to the mortar mixture. Mix for 30 seconds. FIG. 15 shows the mortar mixture after mixing. It can be seen that liquid is concentrated in the middle. Repeat Step 4. FIG. 16 shows the mixture after mixing the second time. The consistency of the mixture should be approximately that of dough.

Figure 17:
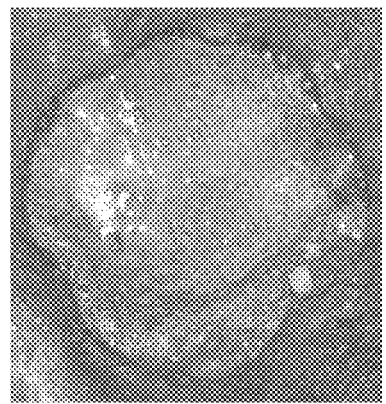
FIG. 17 shows an illustrative embodiment of a mortar mixture after first mixing (e.g. Step 7)
Figure 18:
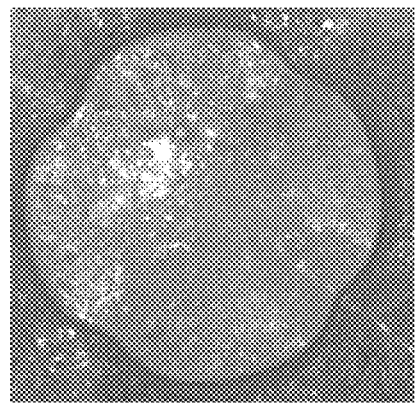
FIG. 18 shows an illustrative embodiment of a mortar mixture after second mixing (e.g. Step 7, Syrup Stage)

7) Pour the remaining water, HRWR, and CNF mixture (one quarter of the total mixture) in the mortar mixture. Mix for 30 seconds. FIG. 17 shows the mortar mixture after mixing. It can be seen that liquid is concentrated in the middle. Repeat Step 4. FIG. 18 shows the mixture after mixing the second time. The consistency of the mixture should be approximately that of syrup.

8) If the mixture is too stiff, add a very small amount of water and repeat Step 4 until the mixture is the consistency of syrup. A low viscosity level is needed so that the mortar is self-consolidating. It has to flow under its own weight around the already placed meshes without creating any voids.

Figure 19:
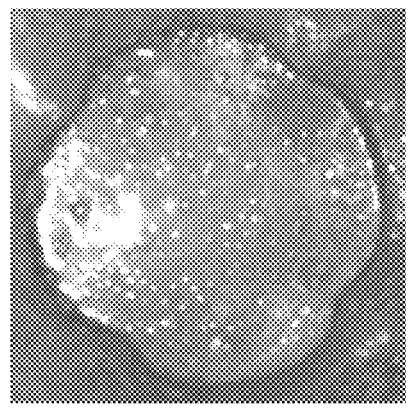
FIG. 19 shows an illustrative embodiment of disproportionate distribution of CNF in mortar.

9) If upon visual inspection there are higher concentrations of CNF in some areas as shown in FIG. 19, additional mixing may alleviate the issue. However, if the concentration on CNF in the mixture is too high, the fibers will clump and additional mixing will not have an effect.

In some embodiments, the concentration of CNF in the CNFA can varied. In some embodiments, a full-scale self-consolidating carbon nanofiber concrete (SCCNFC) column may be utilized.

Test Setup

Figure 20:
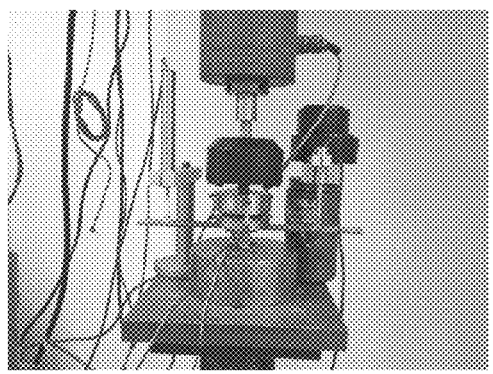
FIG. 20 shows a test setup for strain sensing.
Figure 21:
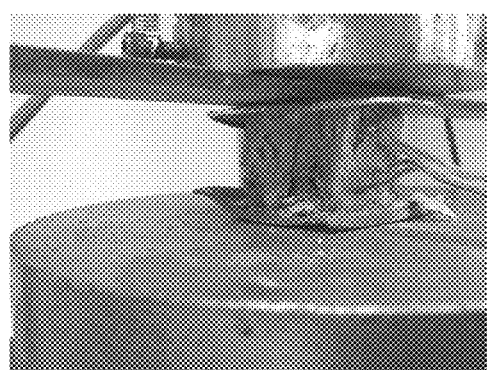
FIG. 21 shows an illustrative embodiment of a tested CNFA.

The test setup used is shown in FIG. 20. Each CNFA was placed in loading frame with a 10 kip capacity. A lead sheet was placed above and below the aggregate to ensure an even contact surface. A steel plate was placed on top of the upper lead sheet. Two linear variable differential transformers (LVDTs) were connected to the steel plate to measure the average displacement of the CNFA during the test. The CNFA was tested in compression at a constant displacement rate of 0.0254 mm/min. (0.001 in./min.) until failure. The electrical resistance was measured using the four probe method on a Keithley Source Meter. FIG. 21 shows a tested CNFA. The CNFA exhibits extensive cover spalling. The specimens were cured for 28 days. After 28 days, the specimens were air dried for 24 hours. To remove all access moisture, they were oven dried for 24 hours at 100° C. (212° F.).

Test Results

Figure 22:
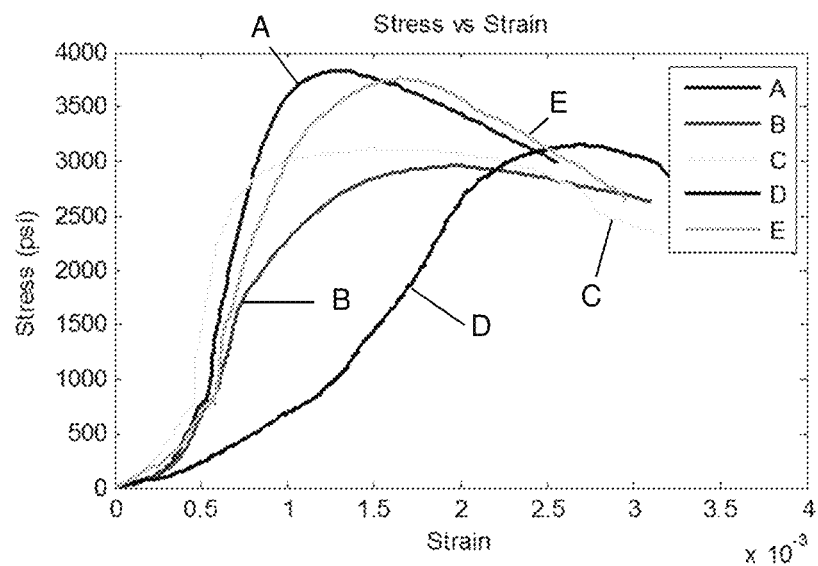
FIG. 22 shows stress v. strain results for 5 CNFA samples (0.7% CNF by weight)

Five CNFA were tested in this study containing 0.70% CNF by weight of cement. The stress verses strain diagram for the five specimens is shown in FIG. 22. It can be seen that there is variation in the stress strain curves of the specimens despite the fact that the specimens were all cast at the same time using the same mix and cured under the same conditions. This is likely due to the fact that the specimens are quite small. Any type of local damage has great effect on the global specimen. Larger specimens are likely to have a more smeared global response to a local phenomenon.

Figure 23:
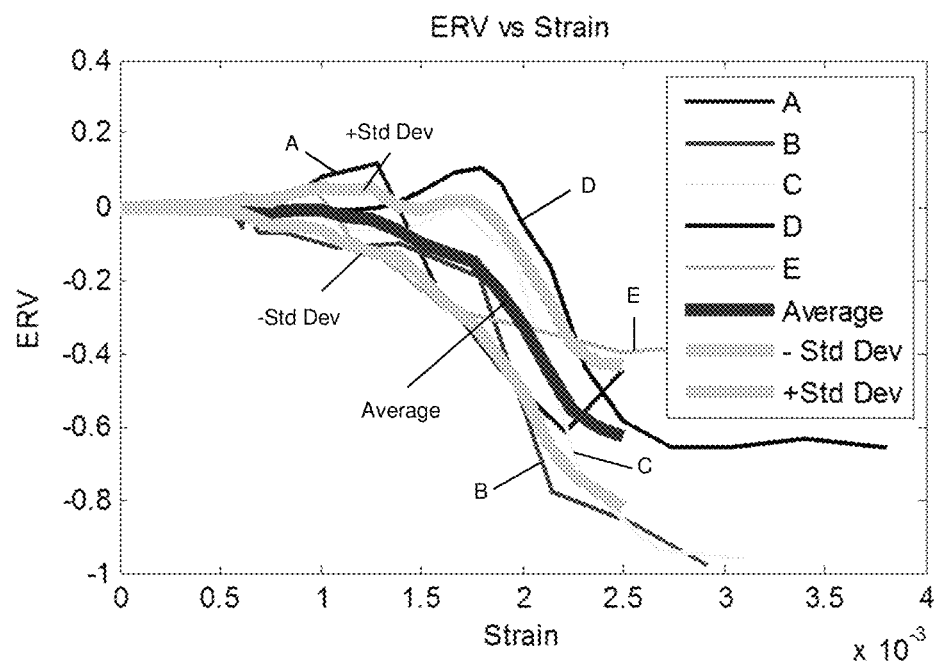
FIG. 23 shows ERV v. strain results various samples.

FIG. 23 shows the electrical resistance variation (ERV) verses strain data for all of the specimens. A strong trend is evident in all of the specimens as shown by the inverted S-shape. While the CNFA are compressed, initially there is very little damage and very little change in ERV. When the mortar begins to crush, the CNF come in better contact with each other, causing the electrical resistance to decrease. As cracks form in the CNFA, the fibers pull out, causing the change in ERV to lessen. These three phenomenon cause the inverted S-shape. By monitoring ERV, the CNFA may allow for early crack detection when a decrease in ERV is detected.

Water Content Test Setup

Figure 24:
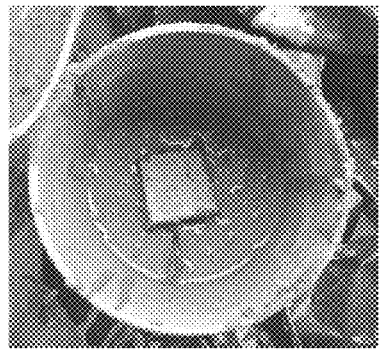
FIG. 24 shows an uncoated CNFA placing in fresh SCC in a cylinder.

In addition to monitoring strain, uncoated CNFA can also monitor the water content of the concrete in which they are embedded. For strain monitoring testing, the CNFA was waterproofed so the only factor affecting the electrical resistance is strain. However, uncoated CNFA are very sensitive to water. Six uncoated specimens were placed in fresh self-consolidating concrete (SCC) as the SCC was being placed in 76.2 mm (3.00 in.) by 152.4 mm (6.00 in.) cylinder molds. Each specimen was placed in the center of the cylinder as shown in FIG. 24.

Water Content Test Results

Figure 25:
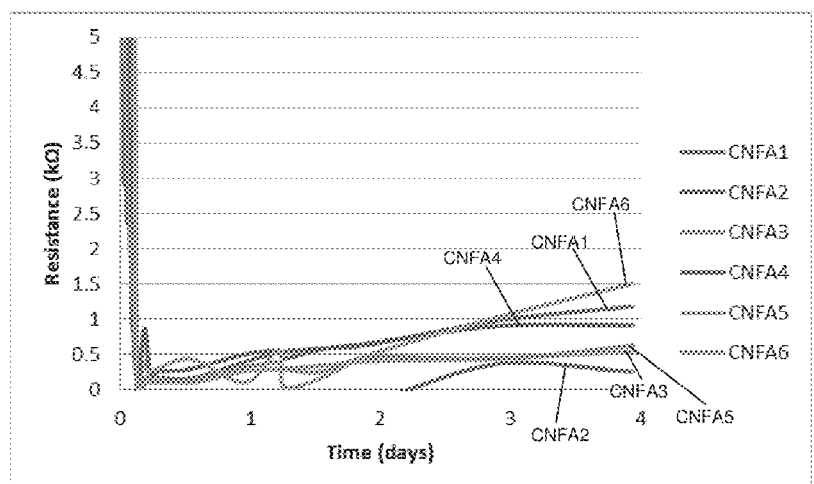
FIG. 25 shows resistance v. time results for CNFA placed in SCC.

The electrical resistance of the embedded uncoated CNFA was monitored using the four probe method on a Keithley Source Meter over a four day period. The initial resistance values were in the Mega Ohm range. Within half an hour of being embedded, all six CNFA had resistances on the order of 0.1 kΩ Over the next four days, the electrical resistance increased as the hydration process took place in the cylinders. These trends can be easily observed in FIG. 25. Monitoring the CNFA for a significant decrease in resistance may allow the presence of moisture to be detected.

Monitoring the water content in the concrete is useful because it indicates the level of hydration in the concrete. The level of hydration in turn correlates to the strength of the concrete. This is useful for such applications as prestressed concrete where a certain strength is required before the prestressing tendons can be released. Currently prestressing plants typically use thermocouples to measure the heat of hydration in the concrete. The CNFA has the potential to be a much more sophisticated means of determining the level of hydration.

Specimen Construction

Figure 26:
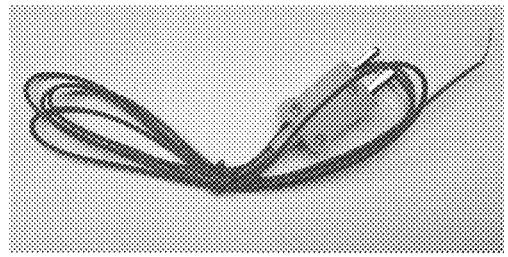
FIG. 26 shows an illustrative embodiment of a thermocouple.
Figure 27:
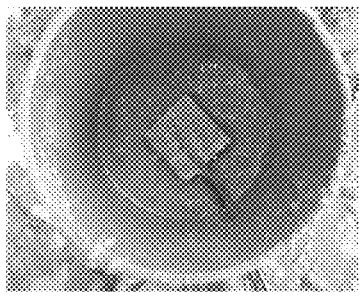
FIG. 27 shows CNFA placed in fresh SCC.

The goal of the experiment was to measure how the electrical resistance of an embedded CNFA varies with temperature. Six CNFAs were embedded in 7.62 cm (3 in.) by 15.24 cm (6 in.) cylinders. Type K thermocouples, as shown in FIG. 26, were embedded in three of the cylinders. A hole was drilled in the center of the cylinder molds to allow the CNFA and thermocouple wires to exit the concrete. Each mold was filled halfway with self-consolidating concrete (SCC), the CNFA was placed in the fresh SCC, and more SCC was placed on top. If the cylinder also contained a thermocouple, the thermocouple was epoxied to the top of the CNFA. SCC was used because it required no mechanical vibrations. Vibrations may cause the CNFA's orientation to change and the cylinder could not have been used for future strain monitoring tests. FIG. 27 shows an uncoated CNFA and thermocouple placed in fresh SCC.

Experimental Setup and Results

Figure 28:
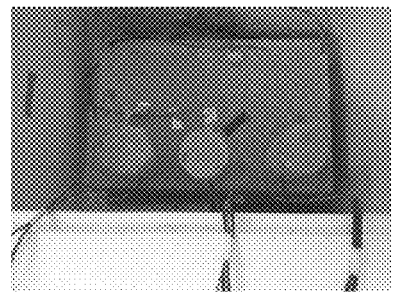
FIG. 28 shows cured concrete cylinders containing CNFAs placed in a freezer.
Figure 29:
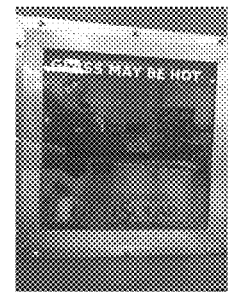
FIG. 29 shows cured concrete cylinders containing CNFAs placed in an oven.
Figure 30:
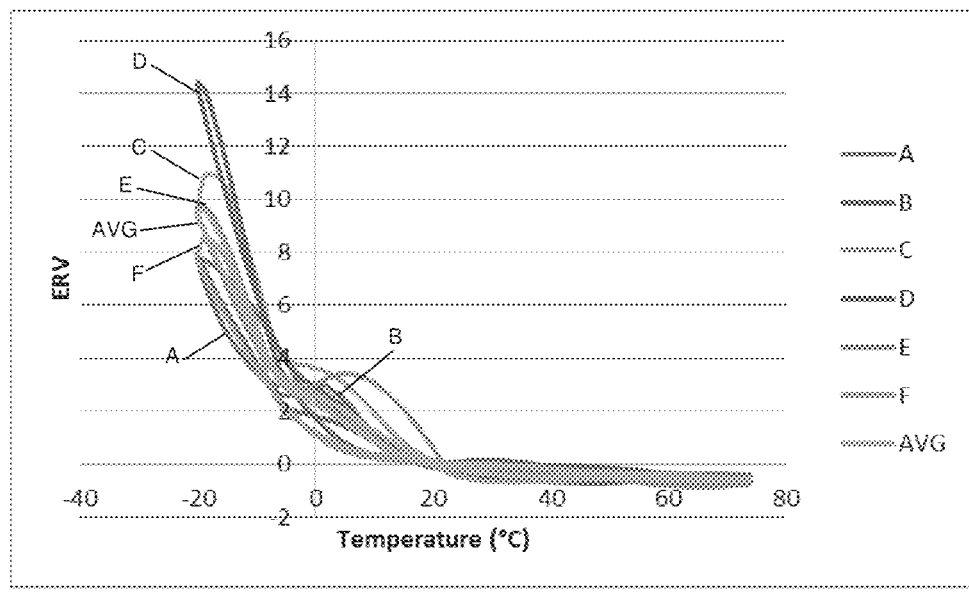
FIG. 30 shows temperature v. ERV results for the cylinder containing CNFA and their average.

Type III cement was used to make the SCC, which has a curing time of seven days. After curing, the temperature study commenced. The initial resistance was measured at the ambient temperature of 21.7° C. (71.1° F.). Six specimens were placed in a freezer capable of reaching −20° C. (−4° F.), as shown in FIG. 28. The specimens were monitored as they were frozen to the minimum temperature and returned to the ambient temperature outside of the freezer. The specimens were then placed in an oven capable of reaching 90° C. (194° F.), as shown in FIG. 29. The specimens were monitored as they were heated to the maximum temperature and returned to the ambient temperature outside of the oven; therefore, the specimens were monitored through one complete cooling and heating cycle. FIG. 30 shows the electrical resistance variation (ERV), defined as the change in electrical resistance divided by the initial electrical resistance, versus the temperature. The initial resistance was taken as the resistance corresponding to 20° C. (68° F.). It is obvious from the figure that the ERV heating and cooling behavior is quite reversible and repeatable across multiple CNFAs. Further, ERV changes may be utilized to monitor temperature changes.

Modeling of Thermal Behavior

The Steinhart-Hart equation (Steinhart & Hart, 1968) is a nonlinear model widely used for the approximation of the resistance/temperature curve of thermistors, $$\frac{1}{T} = A + B\ln(R) + C\ln(R)^3,$$ Equation 1 where:
T: Temperature in Kelvin,
R: Resistance in Ohms,
A, B, C: Steinhart-Hart coefficients.
Often the inverse of the equation is useful, $$R = \exp(\sqrt[3]{x-y} - \sqrt[3]{x+y}),$$ Equation 2 where:
R: Resistance in Ohms, $$x: \sqrt{\left(\frac{B}{3C}\right)^3 + y^2}$$

$$y: \frac{A - \frac{1}{T}}{2C}$$

T: Temperature in Kelvin,
A, B, C: Steinhart-Hart coefficients.
To find the Steinhart-Hart coefficients, at least three operating points are needed denoted by subscripts 1, 2, and 3, $$A + B\ln(R_1) + C\ln(R_1)^3 = \frac{1}{T_1}, \quad \text{Equation 3}$$

$$A + B\ln(R_2) + C\ln(R_2)^3 = \frac{1}{T_2},$$

$$A + B\ln(R_3) + C\ln(R_3)^3 = \frac{1}{T_3},$$

where:

$T_1$, $T_2$, $T_3$: Three different temperatures in Kelvin, $R_1$, $R_2$, $R_3$: Resistance in Ohms corresponding to $T_1$, $T_2$, and $T_3$, A, B, C: Steinhart-Hart coefficients.

Using the relationships and definitions shown in Equation 3, the Steinhart-Hart coefficients can be derived, $$L_1 = \ln(R_1), \quad \text{Equation 4}$$
$$L_2 = \ln(R_2),$$
$$L_3 = \ln(R_3),$$

$$Y_1 = \frac{1}{T_1}, \quad \text{Equation 5}$$
$$Y_2 = \frac{1}{T_2},$$
$$Y_3 = \frac{1}{T_3},$$

$$\gamma_2 = \frac{Y_2 - Y_1}{L_2 - L_1}, \quad \text{Equation 6}$$
$$\gamma_3 = \frac{Y_3 - Y_1}{L_3 - L_1},$$

$$C = \left(\frac{\gamma_3 - \gamma_2}{L_3 - L_2}\right)(L_1 + L_2 + L_3)^{-1}, \quad \text{Equation 7}$$

$$B = \gamma_2 - C(L_1^2 + L_1 L_2 + L_2^2), \quad \text{Equation 8}$$

$$A = Y_1 - (B + L_1^2 C)L_1. \quad \text{Equation 9}$$

Several different operating temperatures were tried in the equations to optimize the fit. The chosen operating temperatures were −10.3° C. (13.5° F.), 21.7° C. (71.1° F.), and 73.9° C. (165.0° F.). The Steinhart-Hart coefficients A, B, and C were determined to be 3.60E-3, 2.19E-4, and 8.16E-5, respectively. Therefore, the best fit equation is:

$$\frac{1}{T} = 3.60 \times 10^{-3} + 2.19 \times 10^{-4} \ln(R) + 8.16 \times 10^{-5} \ln(R)^3, \quad \text{Equation 10}$$

where:

T: Temperature in Kelvin,

R: Resistance in Ohms.

Figure 31:
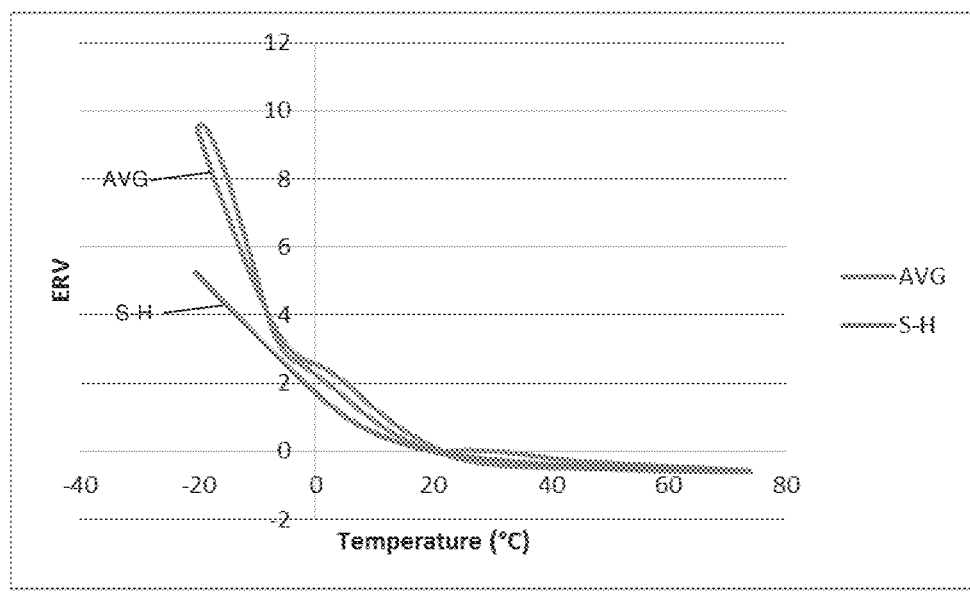
FIG. 31 shows a comparison of the Steinhart-Hart equation and average measure ERV v. temperature for embedded CNFAs.

The coefficient of determination ($R^2$) value for the fit was calculated to be 0.555. The resistance values determined using Equation 10 were converted to ERV values by assuming that the resistance associated with 20° C. (68° F.) was the initial resistance. FIG. 31 shows a comparison of the Steinhart-Hart equation (S-H) and the average measured ERV (AVG) temperature versus ERV relationship. The Steinhart-Hart equation models the behavior for temperatures warmer than about −3° C. (27° F.).

To increase the accuracy of the fit, Steinhart and Hart (Steinhart & Hart, 1968) suggest adding a fifth-order term to their third-order equation. Adding a fifth-order term would greatly complicate the equation and make it impractical for use. Cornell's Creative Machines Lab developed a free mathematical software, Eureqa, which determines mathematical equations that describe sets of data in their simplest form (Schmidt & Lipson, 2009). The average ERV and temperature data were entered into Eureqa and Equation 11 was developed. Equation 11 is both much simpler than Equation 10 and fits the data better with a coefficient of determination of 0.927. FIG. 32 repeats FIG. 31 with the addition of the Eureqa best fit equation (FIT). The equation developed using Eureqa fits the data nearly perfectly. Therefore, the suggested model for the thermal behavior of CNFAs is:

$$\text{ERV} = 2.54\exp(-0.0681T) - 0.578, \quad \text{Equation 11}$$

where:

ERV: Electrical resistance variation,

T: Temperature in Celsius.

Test Specimens

A series of shear- and flexure-critical reinforced concrete (RC) columns were designed for the purpose of studying the applicability of using CNF cement-based composites for structural health monitoring in full-scale structures. The results shown will be limited to one of the flexure-critical columns to show that the CNFAs can be used for structural health monitoring.

Figures 34A, 34B:
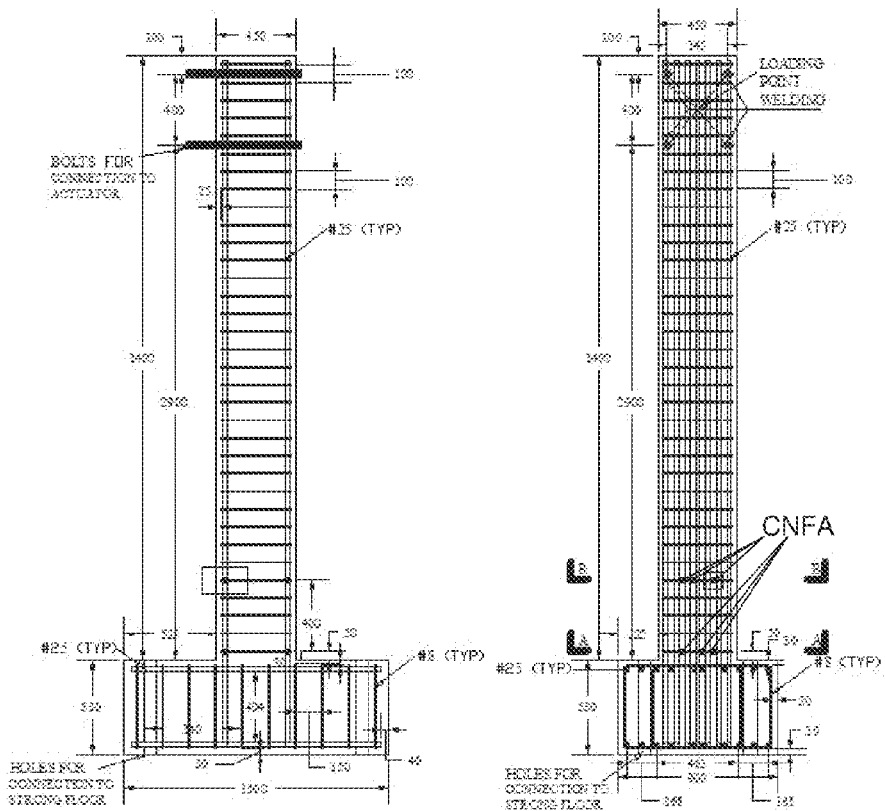
FIGS. 34A-34B show illustrative embodiments of column and foundation elevation views (in mm)

Table 1 shows the geometric and material properties of the rebar used. The cross-section of the column was 450 mm (17.7 in.) square and contained 14 #25 longitudinal rebar, providing a longitudinal reinforcement ratio of 2.91% by volume of concrete. The column also contained #8 stirrups with a spacing of 100 mm (3.94 in.). This corresponds to the maximum spacing specified by the American Concrete Institute (ACI) for columns in seismic regions. This maximum spacing is defined as the distance from the extreme compression fiber to the centroid of the longitudinal tension reinforcement divided by four (ACI Committee 318, 2011). This resulted in a transverse reinforcement ratio of 0.356% by volume of concrete. See FIG. 33 for the column cross-section. The column was 3.13 m (10.27 ft.) tall, resulting in an aspect ratio of 7.75. The column was rigidly connected to a 900 mm (35.4 in.) by 1525 mm (60.0 in.) by 500 mm (19.7 in.) foundation. CNFAs 110 are positioned in the column between #25 bars 120 with wires 130 from the CNFAs extending out of the column. The foundation was reinforced with 20 #25 bars 120 in the loading direction and #8 stirrups 130 spaced at 150 mm (5.91 in.). Strain gauges 150 were positioned in the column for testing purposes; however, strain gauges are not needed as the CNFAs provide strain detection. The foundation and column elevation is shown in FIGS. 34A-34B, and the foundation plan view is shown in FIG. 35. The column was instrumented with 12 CNFAs, among other sensors, as shown in FIG. 33 and FIGS. 34A-34B.

TABLE 1

European Rebar Sizes Used in Column Construction

| European Size | Yield Strength MPa (ksi) | Mass per Unit Length kg/m (lb./ft.) | Nominal Diameter mm (in.) | Cross-Sectional Area $mm^2$ ($in.^2$) |
|---|---|---|---|---|
| 8 | 235 (34.1) | 0.395 (0.265) | 8.00 (0.315) | 50.3 (0.0780) |
| 25 | 335 (48.6) | 3.86 (2.59) | 25.0 (0.984) | 491 (0.761) |

Specimen Construction and Internal Sensor Instrumentation

Figure 36:
FIG. 36 shows column rebar cages and foundations.
Figure 37:
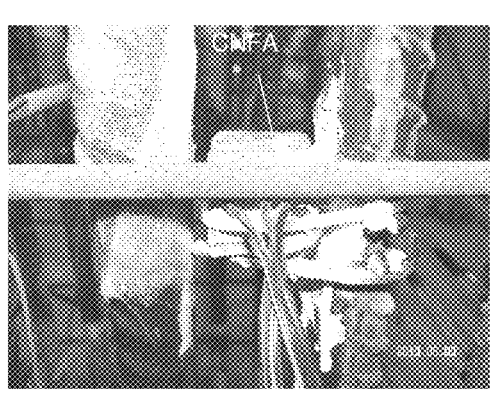
FIG. 37 shows an installed CNFA.
Figure 38:
FIG. 38 shows installed thermocouples and strain gauges.

Several of the foundations for the series of columns were poured simultaneously. FIG. 36 shows column rebar cages and foundations for four flexure-critical and four shear-critical columns. After the rebar cages were built and the foundations poured, the column was instrumented with internal sensors. The rebar adjacent to the CNFA locations shown in FIG. 33 and FIGS. 34A-34B were painted with epoxy so that the electrical properties of the rebar would not affect the electrical properties of the CNFAs. The CNFAs were fixed to the rebar using plastic zip ties. FIG. 37 shows an installed CNFA. The column was also instrumented with strain gauges and thermocouples as shown in FIG. 38.

Loading Procedure

Figure 39:
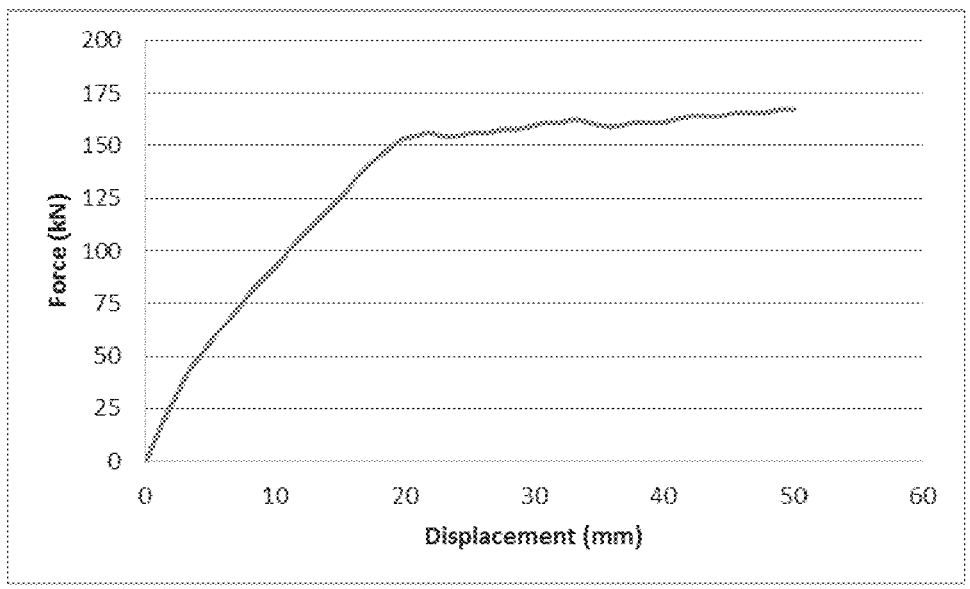
FIG. 39 shows predicted column behavior under monotonic load.

An open-source finite element analysis (FEA) program, Open System for Earthquake Engineering Simulation (OpenSees) (McKenna & Fenves, 1999) was used to model the column subjected to a monotonic push-over load. The results from the model, shown in FIG. 39, predicted that the yield point should occur at approximately a load of 150 kN (33.7 kips) and a displacement of 20 mm (0.787 in.).

Based from the FEA results, a loading procedure was developed as follows:
1. An incremental load was chosen by dividing the yield load by 6 and multiplying by 0.8. This resulted in an incremental load of 20.0 kN (4.50 kips).
2. Using force-control, three cycles of the incremental load times n were applied to the column where n=1, 2, 3, 4, 5, and 6. One cycle consisted of loading the column to the desired load in the positive direction, loading the column to the desired load in the negative direction, and returning to zero load. The cycles were applied at a rate of 0.1 Hz.
3. To ensure that the yield point was not missed, the loading procedure was switched from force-control to displacement-control. The displacement was increased in the positive direction until yielding.
4. The yield point corresponded to a ductility of $\mu=1$. Three cycles were applied at each ductility level, $\mu=1.1$, 1.2, 1.3, etc., until the force of the envelope curve equaled 80% of the maximum force recorded. One cycle provided for loading the column to the desired ductility level in the positive direction, loading the column to the desired ductility level in the negative direction, and returning to zero displacement. The cycles were applied at a rate of 0.1 Hz.

Experimental Setup

To measure the electrical resistance, the outer wires of the six CNFAs were connected in series with a 10 k$\Omega$ resistor and a 10 V power supply, as shown in FIG. 40. The voltage drops across the inner wires of the CNFAs and the resistor were measured using a data acquisition system. There was an impedance problem within the data acquisition system, so differential amplifiers were placed between each component of the circuit and the data acquisition system.

The differential amplifier circuit is shown in FIG. 41. A differential amplifier is a circuit that computes the differences of two voltages and multiplies it by a constant. If all four of the resistors have equal resistances, then the output voltage will equal the difference of the two input voltages. The differential amplifiers, comprising all equal resistors and operational amplifiers, are shown in FIG. 42.

The column foundation was bolted to the strong floor, and a horizontal actuator bolted to a strong wall provided the horizontal loading on the column. Displacement was measured using linear variable differential transformers (LVDTs). The experimental setup is shown in FIG. 43.

Experimental Results

Figure 44:
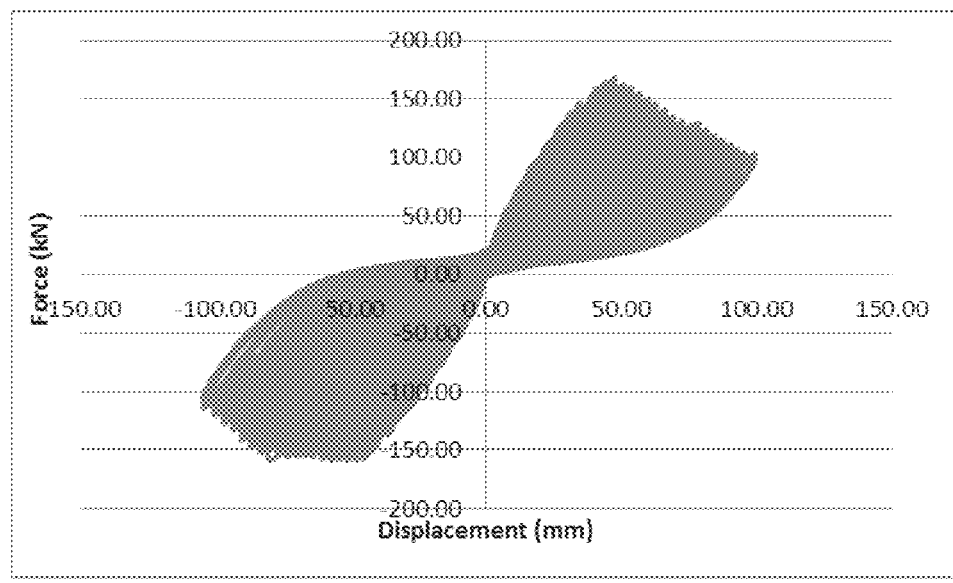
FIG. 44 shows column force v. displacement results.
Figure 45:
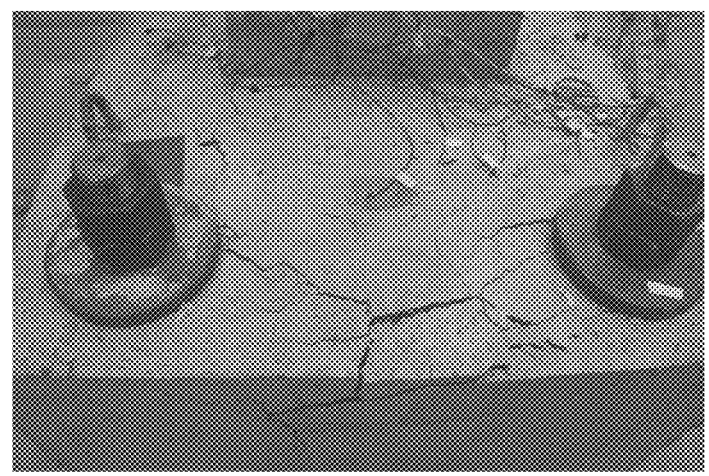
FIG. 45 shows column foundation failure.

FIG. 44 shows the force versus displacement curve for the tested column. The foundation of the column failed rather than the column, as shown in FIG. 45. Because of this failure mode, the column exhibited less ductility than was expected.

Figures 46A, 46B, 46C:
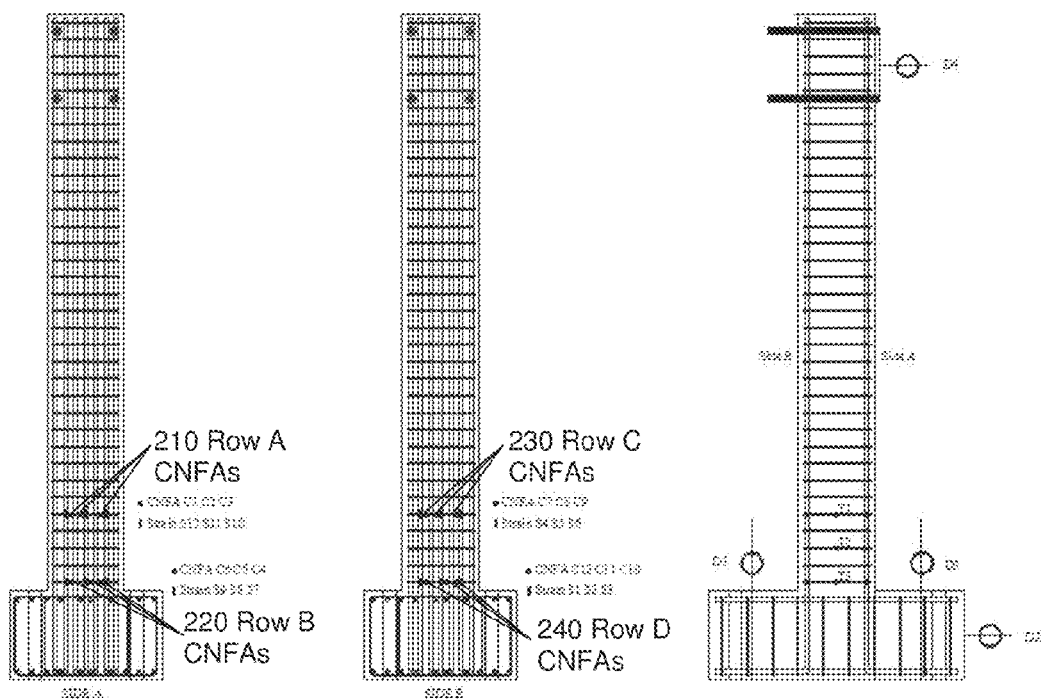
FIGS. 46A-46C show a side a, side b, and front view of column internal sensor locations.
Figures 47A, 47B, 47C:
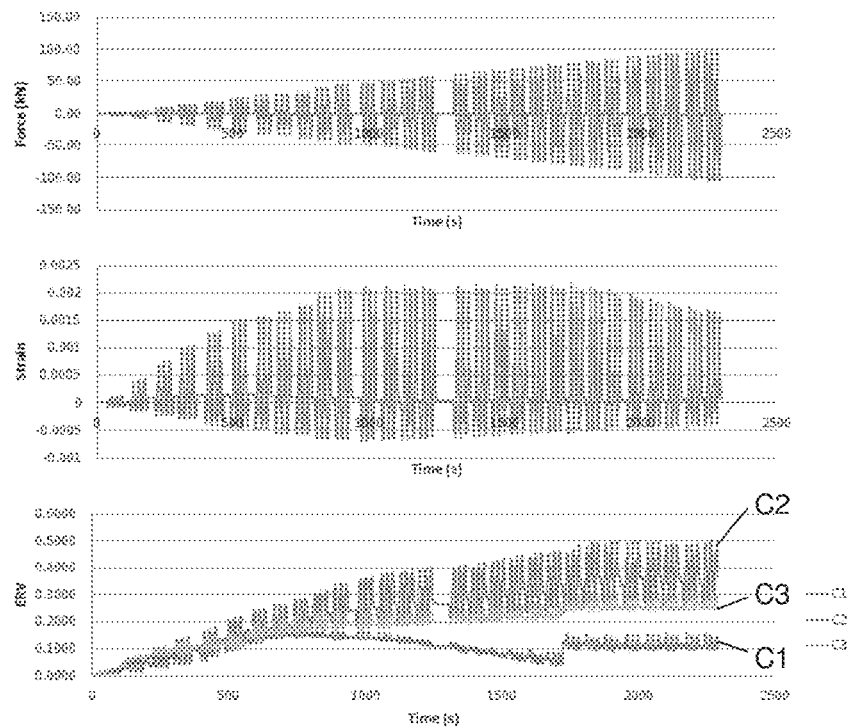
FIGS. 47A-47C show column row A force, strain, and ERV v. time.
Figures 48A, 48B, 48C:
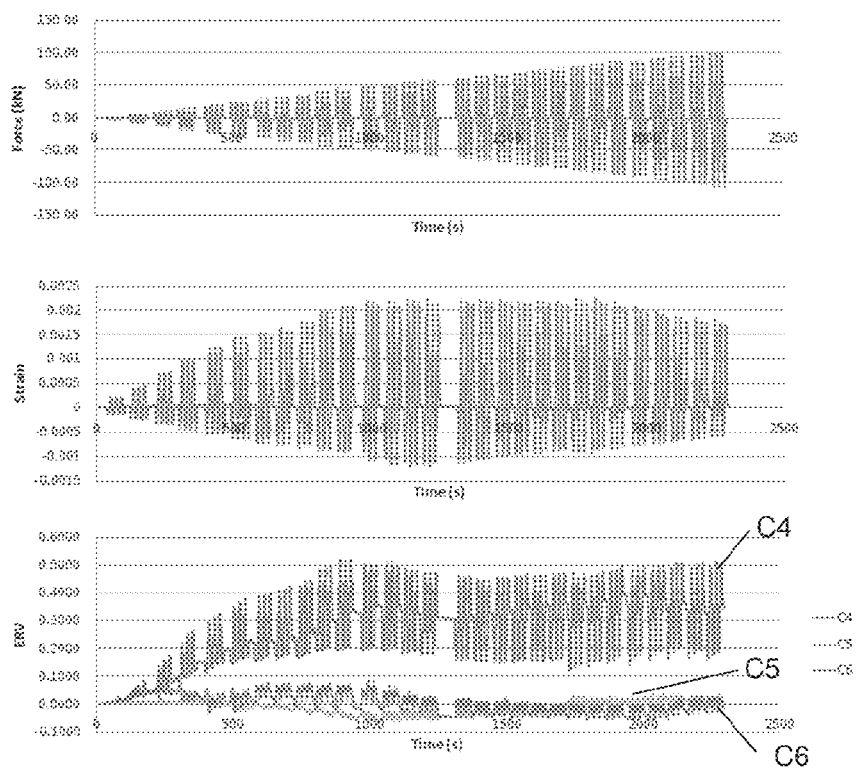
FIGS. 48A-48C show column row B force, strain, and ERV v. time.
Figures 49A, 49B, 49C:
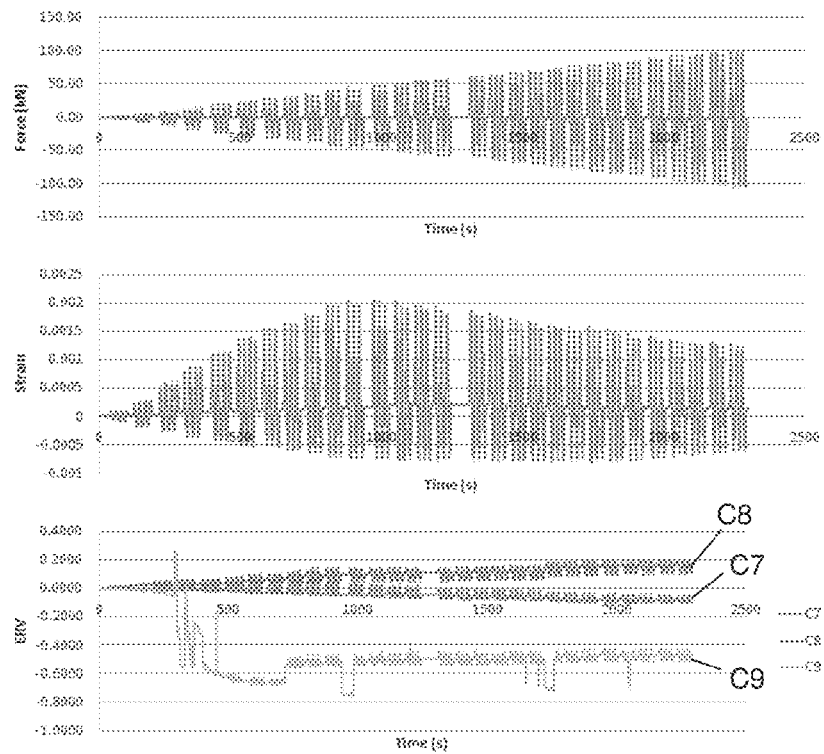
FIGS. 49A-49C show column row C force, strain, and ERV v. time.
Figures 50A, 50B, 50C:
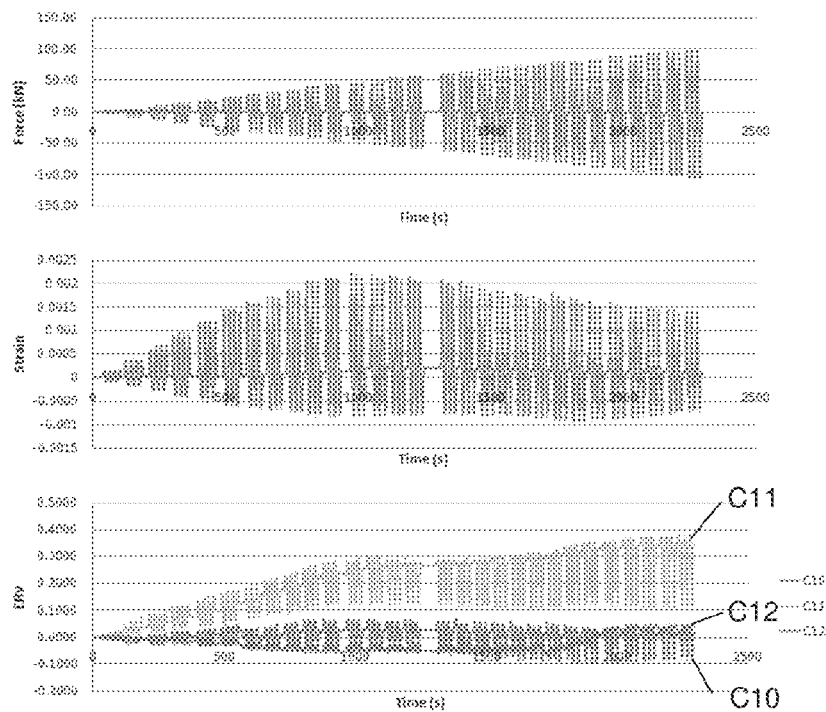
FIGS. 50A-50C show column row D force, strain, and ERV v. time.

When the internal instrumentation was installed, CNFAs and strain gauges were installed in pairs so that the strain and ERV could be directly compared. During the course of the test, three of the strain gauges failed prematurely. The CNFAs were installed in rows of three where each row should have the same strain value. At least one functional strain gauge was located on each row, so the strain values measured by the functional strain gauges were averaged for each row to determine that row's strain. The internal sensor locations are shown in FIGS. 46A-46C for Row A CNFAs 210, Row B CNFAs 220, Row C CNFAs 230, and Row D CNFAs 240. The row designations are shown in Table 2.

TABLE 2

Rows of Equal Strain and Associated CNFAs

| Row | Associated CNFAs | | |
|---|---|---|---|
| A | C1 | C2 | C3 |
| B | C4 | C5 | C6 |
| C | C7 | C8 | C9 |
| D | C10 | C11 | C12 |

Figure 51:
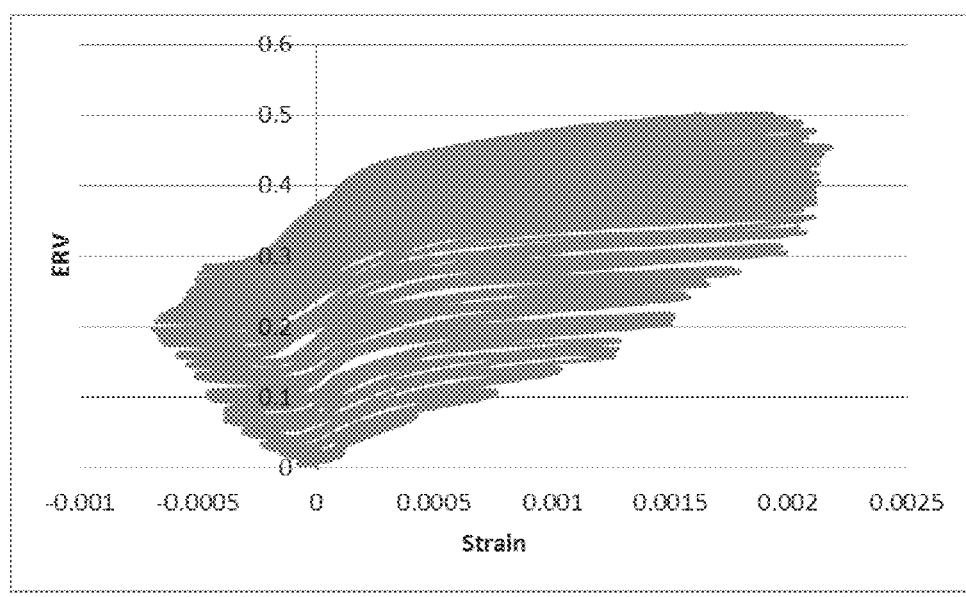
FIG. 51 show the typical stress v. ERV relationship for CNFA embedded in columns.

The force, strain and ERV behavior was compared for each row. Qualitatively, the CNFAs did an excellent job sensing the behavior of the columns illustrating their suitability for structural health monitoring of structures, such as a concrete structure or the like. The CNFAs were not sensitive enough to sense the cyclic behavior of the 20 kN (4.50 kip) load, but with the exception of CNFA C9, each CNFA sensed every other cycle of the entire experiment. CNFA C9 picked up most, but not all, of the cycles. The peaks and valleys of the force, strain, and ERV match for every other CNFA. As shown in FIG. 44, there was a drift behavior in each signal. The drift appears to be random and could not be modeled. FIGS. 47A-47C, 48A-48C, 49A-49C, 50A-50C show the force, strain, and ERV behavior for Rows A, B, C, and D, respectively. FIG. 51 shows a typical strain verses ERV curve for one of the embedded CNFAs. The overall shape of the curve is similar to that shown in FIG. 44 for the cyclically tested cylinder.

Implementations described herein are included to demonstrate particular aspects of the present disclosure. It should be appreciated by those of skill in the art that the implementations described herein merely represent exemplary implementation of the disclosure. Those of ordinary skill in the art should, in light of the present disclosure, appreciate that many changes can be made in the specific implementations described and still obtain a like or similar result without departing from the spirit and scope of the present disclosure. From the foregoing description, one of ordinary skill in the art can easily ascertain the essential characteristics of this disclosure, and without departing from the spirit and scope thereof, can make various changes and modifications to adapt the disclosure to various usages and conditions. The implementations described hereinabove are meant to be illustrative only and should not be taken as limiting of the scope of the disclosure.

What is claimed is:

1. A system for monitoring a structure comprising:
a carbon nanofiber aggregate (CNFA) formed from a mixture of cement, aggregate, high-range-water reducer, and carbon nanofibers (CNF), and a CNF concentration in the CNFA is in a range equal to or between 0.5 and 1.0% by weight,
a plurality of metallic meshes positioned in the CNFA, wherein each of the plurality of metallic meshes are positioned parallel to each other;
a wire coupled to each of the plurality of metallic meshes; and
a data acquisition system, wherein a resistance between two of the plurality of metallic meshes is monitored by the data acquisition system to detect moisture, wherein further a voltage drop between two of the plurality of metallic meshes is monitored by the data acquisition system to determine an electrical resistance variation (ERV), where the ERV is $(R_i-R_0)/R_i$ with Ri representing a resistance at step i and $R_0$ representing an initial resistance, and changes in the ERV are monitored to detect changes in temperature.

2. The system of claim 1, wherein the plurality of metallic meshes provide four metallic meshes.

3. The system of claim 2, further comprising a power source providing current to two of the four metallic meshes.

4. The system of claim 3, further comprising a voltmeter coupled remaining metallic meshes of the four metallic meshes, wherein the voltmeter measures a voltage drop.

5. The system of claim 1, wherein a CNF concentration in the CNFA is 0.7% by weight.

6. The system of claim 1, wherein the CNFA further comprises a pozzolanic material.

7. The system of claim 1, wherein changes in the ERV are monitored to detect strain.

8. A method for monitoring a structure comprising:
positioning a carbon nanofiber aggregate (CNFA) in a concrete structure, wherein the CNFA comprises a mixture of cement, aggregate, high-range-water reducer, and carbon nanofibers (CNF);
a first pair of metallic meshes positioned in the CNFA, wherein the first pair of metallic meshes are positioned parallel to each other;
a second pair of metallic meshes positioned in the CNFA, wherein the second pair of metallic meshes are positioned parallel to each other;
a wire coupled to each of the first pair of metallic meshes and the second pair of metallic meshes;
applying a current to the first pair of metallic meshes;
monitoring a voltage change between the second pair of metallic meshes;
determining a resistance based on the voltage change between the second pair of metallic meshes;
monitoring the resistance between the second pair of metallic meshes for a decrease in the resistance to detect moisture;
determining an electrical resistance variation (ERV), where the ERV is $(R_i-R_0)/R_i$ with Ri representing a resistance at step i and $R_0$ representing an initial resistance; and
monitoring changes in the ERV to detect changes in temperature.

9. The method of claim 8, wherein a CNF concentration in the CNFA is 0.7% by weight.

10. The method of claim 8, wherein a CNF concentration in the CNFA is in a range equal to or between 0.5 and 1.0% by weight.

11. The method of claim 8, wherein the CNFA further comprises a pozzolanic material.

12. The method of claim 8, further comprising monitoring changes in the ERV to detect strain.

13. A method for forming a carbon nanofiber aggregate (CNFA) comprising:
blending water, a High Range Water Reducer (HRWR), and carbon nanofibers (CNF) to form a first mixture;
blending cement and aggregate to form a second mixture;
combining and blending a first portion of the first mixture with an entirety of the second mixture to form a first stage mixture, wherein a reserved portion of the first mixture that was not combined is set aside;
combining and blending a second portion of the reserved portion of the first mixture with the first stage mixture to form a second stage mixture, wherein a remaining portion of the reserved portion that was not combined is set aside;
combining and blending the remaining portion of the reserved portion with the second stage mixture form a final mixture;
positioning a plurality of metallic meshes in a formwork, wherein each of the plurality of metallic meshes is coupled to a wire, and the plurality of metallic meshes are secured in position by holes provided by the formwork;
pouring the final mixture into the formwork, wherein the final mixture surrounds the plurality of metallic meshes, and the wires coupled to the plurality of metallic meshes extend out of the final mixture; and
curing the final mixture, wherein a CNF concentration in the CNFA is in a range equal to or between 0.5 and 1.0% by weight.

14. The aggregate of claim 13, wherein the plurality of metallic meshes provide four metallic meshes.

15. The aggregate of claim 13, wherein a CNF concentration in the CNFA is 0.7% by weight.

16. The aggregate of claim 13, wherein the CNFA further comprises a pozzolanic material.

* * * * *